United States Patent [19]
Sailor et al.

[11] Patent Number: 5,338,415
[45] Date of Patent: Aug. 16, 1994

[54] METHOD FOR DETECTION OF CHEMICALS BY REVERSIBLE QUENCHING OF SILICON PHOTOLUMINESCENCE

[75] Inventors: Michael J. Sailor, La Jolla; Grace Credo; Julie Heinrich, both of San Diego; Jeffery M. Lauerhaas, La Jolla, all of Calif.

[73] Assignee: The Regents of the University of California, Oakland, Calif.

[21] Appl. No.: 901,753

[22] Filed: Jun. 22, 1992

[51] Int. Cl.$^5$ .................. C25F 3/12; H01L 21/306; B44C 1/22; G01J 3/30
[52] U.S. Cl. .................. 204/129.2; 204/129.3; 204/129.75; 156/626; 156/662; 356/318
[58] Field of Search .......... 204/129.3, 129.2, 129.75; 356/317, 318; 156/626, 662

[56] References Cited

U.S. PATENT DOCUMENTS

| | | | |
|---|---|---|---|
| 3,962,052 | 6/1976 | Abbas et al. | 204/129.3 |
| 4,377,436 | 3/1983 | Donnelly et al. | 156/626 |
| 4,874,484 | 10/1989 | Foell et al. | 204/129.3 |
| 5,026,159 | 6/1991 | Allen et al. | 356/318 |
| 5,139,624 | 8/1992 | Searson et al. | 204/129.3 |

FOREIGN PATENT DOCUMENTS

| | | | |
|---|---|---|---|
| 0486873 | 5/1992 | European Pat. Off. | 204/129.3 |
| 0069834 | 6/1981 | Japan | 156/626 |
| 0155724 | 9/1983 | Japan | 156/626 |
| 8401029 | 3/1984 | World Int. Prop. O. | 356/318 |

OTHER PUBLICATIONS

Reversible Luminescence Quenching of Porous Si By Solvents; Jeffrey M. Lauerhaas, et al.; Journal of the American Chemical Society, 1991; pp. 1911-1912.

Silicon Quantum Wire Array Fabrication by Electrochemical and Chemical Dissolution of Wafers; L. T. Canham; Appl. Phys. Lett. 57 (10); Sep. 3, 1990; pp. 1046-1048.

Shine On, Holey Silicon; Ivan Amato; Science, vol. 252; pp. 922-923.

Porous Silicon Formation: A Quantum Wire Effect; V. Lehmann, et al; Appl. Phys. Lett. 58 (8); Feb. 25, 1991; pp. 856-858.

*Primary Examiner*—Donald R. Valentine
*Attorney, Agent, or Firm*—Brown, Martin, Haller & McClain

[57] ABSTRACT

An n-type silicon (Si) wafer is galvanostatically etched in a hydrofluoric acid (HF)-containing solution while being illuminated with a 300 watt tungsten light source to form porous silicon with luminescent properties. Photoluminescence of the porous silicon is monitored using a short wavelength visible or ultraviolet light source and a monochromator/CCD detector assembly. Upon exposure to organic solvents, the photoluminescence is quenched. Within seconds of removal of the solvent, the original intensity is recovered and further exposure of the porous silicon to organic solvents will again result in quenching of the luminescence.

7 Claims, 1 Drawing Sheet

METHOD FOR DETECTION OF CHEMICALS BY REVERSIBLE QUENCHING OF SILICON PHOTOLUMINESCENCE

BACKGROUND OF THE INVENTION

Silicon is known for its ready availability and relative ease in processing for fabrication of electronic devices. It has recently been discovered that by electrochemically and chemically etching single-crystal silicon, nanometer structures are formed which convert the silicon into a highly luminescent material. The "quantum wires" that are formed during the etch photoluminesce in the visible region of the electromagnetic spectrum when illuminated as a result of the increase in effective band gap energy.

While the ability to fabricate photoluminescent silicon has clear implications in the development of optical electronics, other applications are also worthy of exploration.

Many industries, including the electronics industry, utilize a variety of organic solvents and gases which present environmental and/or safety hazards. These solvents can be highly volatile and flammable, and can be toxic and/or carcinogenic to those who are exposed to even relatively low levels of the solvent. Thus, in applications where no alternatives exist for these solvents, it is necessary to provide means for determining whether organic solvents are present in areas which should be free of such hazardous chemicals.

SUMMARY OF THE INVENTION

It is an object of the present invention to provide a device for detecting the presence of organic solvent molecules.

It is another object of the present invention to provide a means for continuously monitoring the presence of organic solvent molecules, where the device is capable of repeated detections.

Still another object of the present invention is to provide a device which is capable of detecting dipolar gases.

In an exemplary embodiment, an n-type silicon (Si) wafer is galvanostatically etched in a hydrofluoric acid (HF)-containing solution while being illuminated with a 300 watt tungsten light source to form porous silicon with luminescent properties. The wafer is rinsed with ethanol and dried under a stream of nitrogen gas.

Photoluminescence of the porous silicon is monitored using a short wavelength visible or ultraviolet light source and a monochromator/CCD detector assembly. Upon exposure to organic solvents, in either liquid or vapor form, the photoluminescence is quenched. Immediately after exposure to the solvent, the emission maximum intensity is significantly decreased, and the corresponding emission maximum wavelength shifts to a shorter wavelength. Within seconds of removal of the solvent, the original intensity is recovered and further exposure of the porous silicon to organic solvents will again result in quenching of the luminescence.

BRIEF DESCRIPTION OF THE DRAWINGS

Understanding of the present invention will be facilitated by consideration of the following detailed description of a preferred embodiment of the present invention, taken in conjunction with the accompanying drawings, in which like reference numerals refer to like parts and in which.

DETAILED DESCRIPTION OF THE PREFERRED EMBODIMENT

Figure 1:
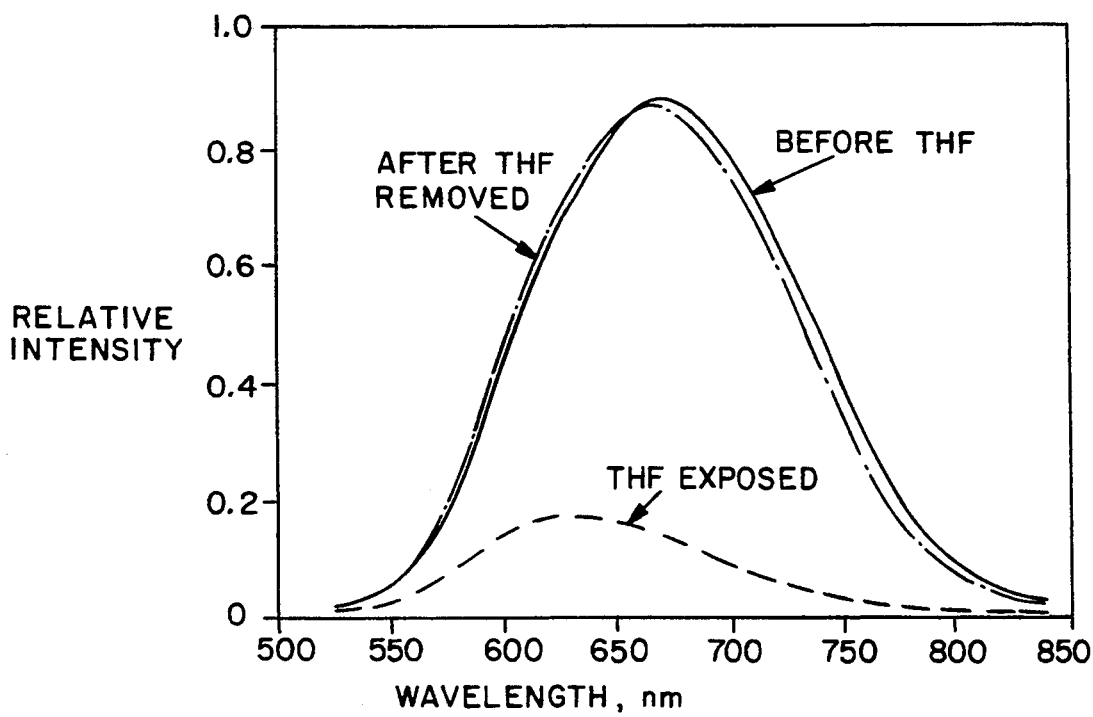
FIG. 1 is a plot of wavelength versus relative intensity of photoluminescence before, during and after exposure of porous silicon to a solvent.

An n-type silicon wafer (0.642 ohm-cm resistivity, (100) orientation) is submersed in a solution of 50:50 ethanol/HF after attaching an electrode to the backside of the wafer. A second electrode is immersed in the bath, and a current is applied to the electrodes such that a low current density is initiated within the solution. The wafer is illuminated with a 300 watt tungsten lamp during etch for approximately 30 minutes at 5 mA/cm$^2$, followed by a 25 second etch at 50 mA/cm$^2$. The wafer is rinsed with ethanol and dried under a stream of nitrogen.

The etch time is not critical, however, resolution improves with longer etch times. The etch time will also impact interference behavior when the porous silicon is excited with white light. In this case, the longer the etch, the longer the wavelength of the false color generated by the interference. The current density need not be exactly 5 mA/cm$^2$, but will be most effective if kept within a factor of 10 of 5 mA/cm$^2$.

The material which is used for formation of porous Si is not limited to single-crystal n-type silicon. P-type silicon wafers can also be used, the resistivity ranges for both p- and n-type running from near intrinsic to just below levels where metallic properties are encountered. Some workers have attained photoluminescence in amorphous silicon, and silicon on sapphire (SOS) or other insulating substrates may also be used.

Exposure wavelengths during electrochemical etch can be derived from any kind of light source. In bulk conversion of silicon to a porous condition, such as may be used for general use detectors of the present invention, longer wavelengths, in the red regions, may be desired for deeper penetration of the etch into the silicon. For better resolution, shorter wavelengths (green, blue, UV) may be desirable.

For practical applications as an environmental monitor, the porous silicon detector is placed in air and monitored using a short visible wavelength or ultraviolet excitation source with a monochromator/CCD detector assembly. For evaluation purposes in laboratory testing, the silicon wafers were placed in a light-transmissive vacuum chamber which was evacuated to 50 mTorr and backfilled with nitrogen three times before analysis. Wafers for vapor analysis were left under vacuum and wafers which were to be directly subjected to neat (liquid) solvent were handled under purified nitrogen, and exposed to the solvent using conventional vacuum line or Schlenk and syringe techniques, as are known in the art. All solvents were purified and deoxygenated according to published procedures (see, e.g., Shriver, D. F., et al., *The Manipulation of Air-Sensitive Compounds,* John Wiley & Sons, New York, 1986, pp. 84–92), and the solvents used in vapor exposure studies were freeze-pump-thaw degassed three times prior to use. The photoluminescence of the porous silicon samples was monitored using a 442 nm He/Cd laser excitation source and a ¼ m monochromator/CCD detector setup. The porous silicon photoluminesces to emit light in the 500 nm to 800 nm wavelength range. The amount of luminescence quenching by each solvent was determined as the relative luminescence intensity directly before and one minute after exposure to the solvent ($I/I_0$).

The emission spectra of a luminescent porous silicon layer before and after exposure to approximately 160 torr of tetrahydrofuran (THF) is illustrated in FIG. 1. Immediately after exposure to the solvent, the emission maximum intensity at 670 nm decreased by a factor of four, and the emission maximum shifted to 630 nm. The emission spectrum recovered to the original intensity within seconds of evacuation of the excess solvent vapor, although the emission maximum at this point has shifted slightly to approximately 660 nm. Repeated THF exposure/evacuation cycles reproduced the latter two spectra. Exposure to gaseous diethyl ether, methylene chloride, toluene, o-xylene, ethanol, and methanol also resulted in reversible quenching.

Figure 2:
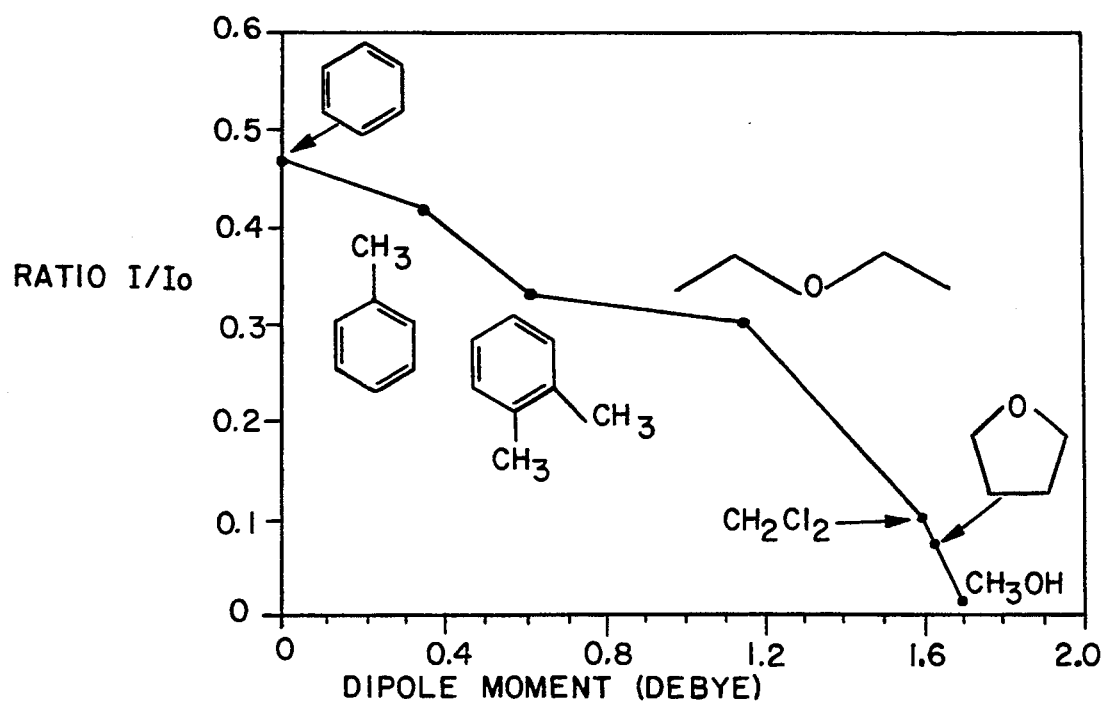
FIG. 2 is a plot of dipole moment versus ratio of luminescence intensity before and after exposure to a solvent.

The correlation of luminescence quenching ratios ($I/I_0$) of the neat solvents to the dipole moments of the gas phase solvents is illustrated in FIG. 2. The relative intensity tracks with the dipole moment of the gases, however, the mechanism of emission quenching is not known. All solvents that were investigated reduced the emission intensity Of porous silicon, indicating that the solvent interactions reduce carrier trapping in silicon. Addition of a toluene solution of the non-polar electron donor ferrocene to a porous silicon wafer immersed in toluene results in a complete loss of luminescence, suggesting that quenching by interfacial electron transfer can also occur.

The correlation between quenching and dipole moment suggests the possibility of using porous silicon detectors for detecting the presence of chemicals or detecting other gaseous materials, or for detecting the presence of chemicals or forces which will affect, interact with or modify the dipole moments of the gaseous molecules.

Generally, the extreme sensitivity of the luminescent porous silicon surface makes it well suited for applications as chemical sensors. A detector assembly based on porous silicon can be made compact by using a solid state laser as an excitation source, or the excitation source may be provided by way of optical fibers.

It will be evident that there are additional embodiments which are not illustrated above but which are clearly within the scope and spirit of the present invention. The above description and drawings are therefore intended to be exemplary only and the scope of the invention is to be limited solely by the appended claims.

We claim:

1. A method for monitoring contamination of an environment by molecules of organic solvent which comprises:

forming porous silicon on a silicon surface wherein said porous silicon photoluminesces upon illumination by laser light in an uncontaminated environment;

positioning said porous silicon in said environment;

illuminating said porous silicon with laser light; and detecting changes in the photoluminescence intensity wherein decreases in the intensity indicate presence of contamination.

2. A method as in claim 1 wherein the step of forming porous silicon comprises:

selecting a substrate having a silicon surface; and electrochemically etching said silicon surface while exposing said silicon surface to a light source.

3. A method as in claim 1 wherein the step of detecting changes in the photoluminescence intensity comprises detecting photoluminescence with a monochromator/CCD detector.

4. A method as in claim 1 wherein said porous silicon emits light having a wavelength in the range of 500 nm to 800 nm during photoluminescence.

5. A method for detecting an organic solvent which comprises:

selecting a single-crystal silicon substrate;

electrochemically etching said silicon substrate in an HF-containing solution while exposing said silicon substrate to a light source to form at least one area of porous silicon on said silicon substrate;

positioning said silicon substrate having said at least one area of porous silicon in an environment in which organic solvent detection is desired;

illuminating said at least one area of porous silicon with laser light;

detecting photoluminescence of said at least one area of porous silicon wherein the photoluminescence will decrease from its maximum value in the presence of said organic solvent.

6. A method as in claim 5 wherein said light source comprises a tungsten lamp.

7. A method as in claim 5 wherein said laser light has a wavelength within the range of green light to ultraviolet light.

* * * * *